(12) United States Patent
Eckermann

(10) Patent No.: US 9,907,546 B2
(45) Date of Patent: Mar. 6, 2018

(54) SURGICAL ELEVATOR WITH SUCTION

(71) Applicant: Jan Eckermann, Bakersfield, CA (US)

(72) Inventor: Jan Eckermann, Bakersfield, CA (US)

( * ) Notice: Subject to any disclaimer, the term of this patent is extended or adjusted under 35 U.S.C. 154(b) by 179 days.

(21) Appl. No.: 14/816,507

(22) Filed: Aug. 3, 2015

(65) Prior Publication Data

US 2016/0206302 A1 Jul. 21, 2016

Related U.S. Application Data

(60) Provisional application No. 62/104,020, filed on Jan. 15, 2015.

(51) Int. Cl.
*A61B 1/32* (2006.01)
*A61B 17/02* (2006.01)

(52) U.S. Cl.
CPC ........ *A61B 17/02* (2013.01); *A61B 2217/005* (2013.01); *A61B 2218/008* (2013.01)

(58) Field of Classification Search
CPC ........ A61B 2217/002; A61B 2217/005; A61B 2217/007

USPC ......................... 600/184, 187, 194, 204, 205
See application file for complete search history.

(56) References Cited

U.S. PATENT DOCUMENTS

| 2011/0060192 A1* | 3/2011 | Pastron ............. A61M 16/0463 |
| | | 600/205 |
| 2011/0112372 A1* | 5/2011 | Hajarian ............... A61M 1/008 |
| | | 600/205 |

* cited by examiner

*Primary Examiner* — Ellen C Hammond
*Assistant Examiner* — Christina Negrellirodriguez
(74) *Attorney, Agent, or Firm* — R. Scott Kimsey, Esq.; Klein DeNatale Goldner

(57) ABSTRACT

A suction elevator with suction capability includes a handle having a first end and a second end. The first end of the handle includes a connector for attaching the surgical elevator to a suction source. An arm extends from the second end of the handle, the arm having a blade portion at the end opposite that which extends from the handle. A continuous bore runs through the connector, handle, and arm, ending where the blade defines an opening in fluid communication with the bore.

8 Claims, 5 Drawing Sheets

SURGICAL ELEVATOR WITH SUCTION

RELATED APPLICATIONS

This application claims priority of U.S. Provisional Patent Application No. 62/104,020, filed Jan. 15, 2015, and entitled "Surgical Elevator with Suction," which application is incorporated herein by reference in its entirety.

BACKGROUND OF THE INVENTION

1. Field of the Invention

The present disclosure relates generally to a surgical elevator device, and more specifically to surgical elevator device with suction capability.

2. Background

Surgical elevators are used for spinal surgery and other surgical processes. Typically, tissue is removed from bone using a suitable cutting tool, such as an electric knife, after which the separated tissue must be elevated, or retracted, away from the bone. A common device used to elevate tissue from the bone is a Cobb elevator.

A typical Cobb elevator includes an elongate handle, which may be knurled or otherwise fabricated to allow for easy gripping of the device. A thin, elongate arm extends from the handle and terminates in a blade, which is typically flattened, widened, and rounded. The blade may also be formed with a slight curvature to allow better manipulation of the tissue around the bone.

During the surgical process, the use of the electric knife or other cutting device, along with the Cobb elevator, requires both hands of the surgeon. Use of additional tools requires the surgeon to release either the knife or the Cobb elevator so that another tool may be selected, or requires a second person to manipulate the additional tool. In a common surgical procedure during which a Cobb elevator is used, one additional tool used is a suction tool. Suction is required because during the cutting process blood and other fluids flow into the surgical site. Further, when an electric knife is used smoke may be generated, and that smoke may reduce visibility at the surgical site.

Neither setting down the electric knife or Cobb elevator, nor having a second individual attempt to use a suction tool, is ideal. By releasing a tool, such as the electric knife, a surgeon is necessarily interrupting the surgical process in order to use suction at the surgical site. Further, the surgeon has to then release the suction tool and retrieve the electric knife, and during that time period blood and fluids begin to once again fill the surgical site. Having a second individual employing suction during surgery can obscure the surgeon's view of the surgical site, result in crowding around the surgeon while surgery is being performed, and render surgery more difficult because of the presence of additional instruments at the site of surgery.

SUMMARY OF THE INVENTION

A suction elevator with suction capability includes a handle having a first end and a second end. The first end of the handle includes a connector for attaching the surgical elevator to a suction source. An arm extends from the second end of the handle, the arm having a blade portion at the end opposite that which extends from the handle. A continuous bore runs through the connector, handle, and arm, ending where the blade defines an opening in fluid communication with the bore.

The surgical elevator may be constructed from a single, unitary piece of material.

The internal diameter of the bore may decrease along the length of the handle.

The internal diameter of the bore may decrease along the length of the arm.

The opening defined by the blade portion of the device may be of substantially the same width as the blade portion.

The bore may branch at or near the blade portion to define a first terminal bore and a second terminal bore. The first terminal bore may be in fluid communication with a first opening defined by the blade portion, and the second terminal bore may be in fluid communication with a second opening defined by the blade portion.

The blade portion may include a first flange at one edge thereof, and a second flange at another edge thereof, the flanges forming a flattened area that flanks a portion of the continuous bore, and that may also flank the opening formed in the blade portion.

The surgical elevator preferably has sufficient rigidity and structural strength to allow a user thereof to separate large muscle groups during a surgical procedure.

The surgical elevator my also include a handle with a first end and a second end and a central bore running therethrough. A connector may be attached to the first end of the handle and may also have a central bore therethrough, the central bore of the connector in fluid communication with the central bore of the handle. An arm may be attached to the second end of the handle, the arm having a central bore running therethrough that is in fluid communication with the central bore of the handle. The arm may define a blade portion that has an opening to the exterior environment of the device, that opening in fluid communication with the exterior environment and the central bore running through the arm.

DETAILED DESCRIPTION OF THE INVENTION

Figure 1:
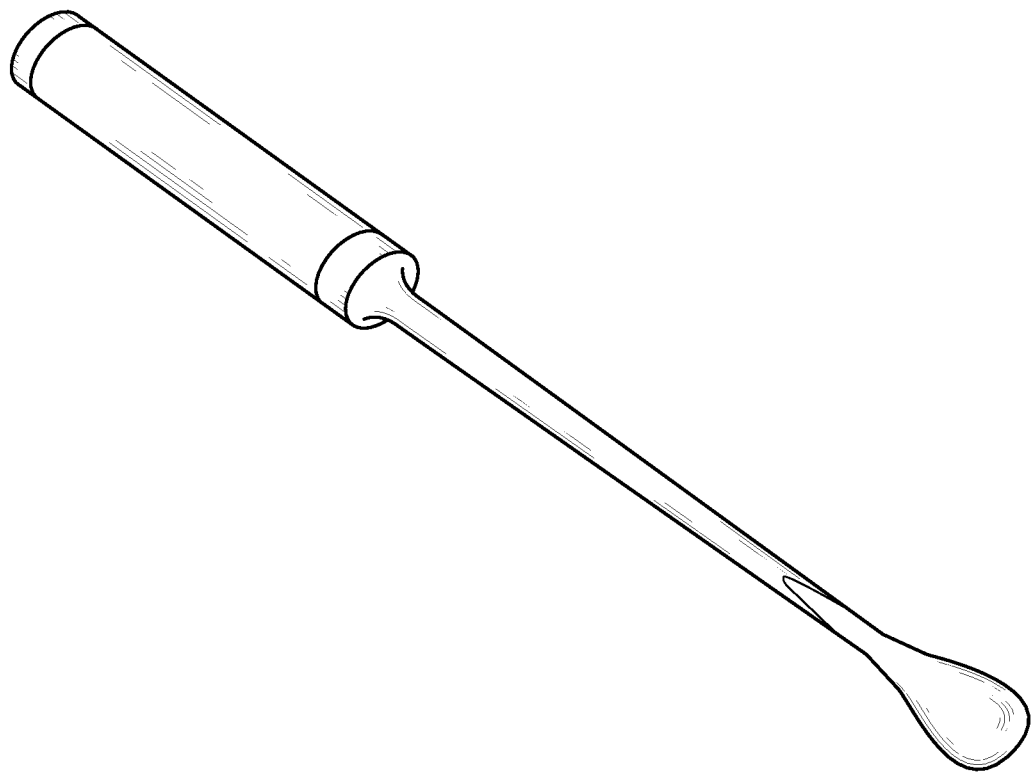
FIG. 1 depicts a prior art Cobb elevator.

FIG. 1 provides an image of a prior art surgical elevator commonly known as a Cobb elevator. It should be noted that Cobb elevators, and surgical elevators generally, may vary in size, shape, and form, and that the principles of the present device disclosed herein may be applied to any suitable device.

Figure 2:
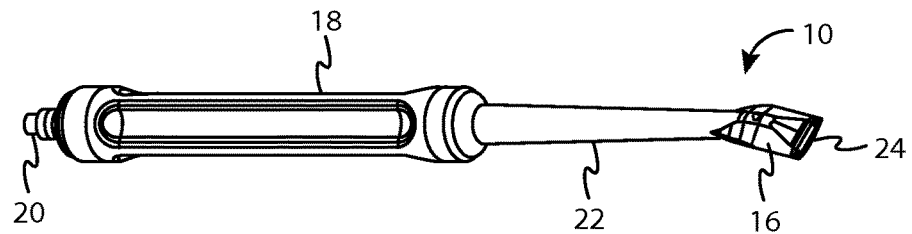
FIG. 2 is a perspective view of one embodiment of a surgical elevator with suction functionality.

FIG. 2 depicts one embodiment of a Cobb elevator with suction functionality. For convenience, the device will be referred to herein as a "suction elevator." Suction elevator 10 includes handle 18, arm 22 extending away from handle 18, and blade 16 forming one end of the device. Suction elevator 10 further includes a central bore 12 extending through handle 18 of suction elevator 10, as well as a central bore 13 extending through arm 22 thereof (the central bores shown, for example, in FIG. 3). Handle 18 may be grooved, as shown in the drawings, or may include knurls on the surface thereof. Any surface texture or structure to facilitate gripping handle may be used or, if desired, the exterior surface of handle 18 may be smooth.

One end of handle 18 includes a connector 20, which has a bore therethrough in fluid communication with central bore 12, connector 20 adapted to connect to a suction line or other suitable structure so that suction may be drawn through a bore in connector 20, and from there through central bore 12. The other end of handle 18 is attached to arm 22, with central bore 12 of handle 18 in fluid communication with central bore 13 of arm 22. Thus, suction drawn through connector 20 is drawn through the entire device, resulting in active suction at opening 24, where central bore 13 terminates at the end of blade 16—the portion of the present device adjacent the surgical site when the present device is in use.

Central bore 12 may have a continuous internal diameter along its length. It is contemplated, however, that the internal diameter of central bore 12 may grow smaller as central bore 12 reaches the end of handle 18 proximal to arm 22. The presence or absence of such a constriction, as well as the degree of constriction, affects the speed of air flow at a given point within suction elevator 10. Likewise, as shown in the drawings, central bore 13 may increase in internal diameter as it nears the end of arm 22 that forms blade 16. It is contemplated, however, that central bore 13 may also have a consistent internal diameter along the length of arm 22 until it reaches blade 16, whereupon the bore may take on a variety of shapes and configurations, as described in greater detail below.

Figure 3:
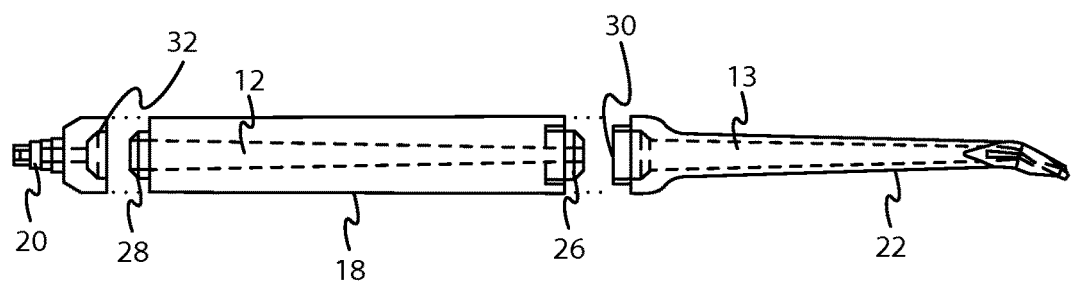
FIG. 3 is an exploded view of one embodiment of a surgical elevator with suction functionality, with internal bored represented by dashed lines.

In the embodiment of the present device shown in FIGS. 2 and 3, central bore 13 forms an elongate, flattened opening 24 at the tip of blade 16, such that opening 24 extends substantially across the width of blade 16. This provides a relatively wide suction area at the point at which suction elevator 10 contacts the surgical site.

Figure 4:
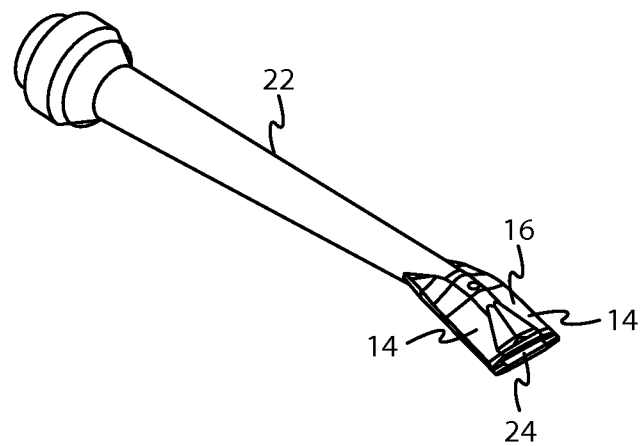
FIG. 4 is a perspective view of the arm of one embodiment of a surgical elevator with suction functionality.

FIG. 4 provides a perspective view of arm 22 of the embodiment of suction elevator 10 shown in FIGS. 2 and 3, arm 22 shown terminating in the wider, flatter blade 16 with opening 24 at the tip thereof. Also more clearly shown in FIG. 4 (and in FIG. 5, described below) are flanges 14 along the edges of blade 16. Flanges 14 are simply flat, relatively sharp edges that allow the present device to penetrate and manipulate tissue more readily than a conventional elevator, which is more rounded along its edges. Various angles of the blade 16 of the present elevator may also be adjusted, changing the profile of blade 16 such that it is better suited to a variety of uses. Although it is preferred that the flattened flanges 14 flank bore 13 and opening 24 of blade 16, it is contemplated that in some embodiments of the present invention more rounded or otherwise shaped edges may be provided.

Figure 5:
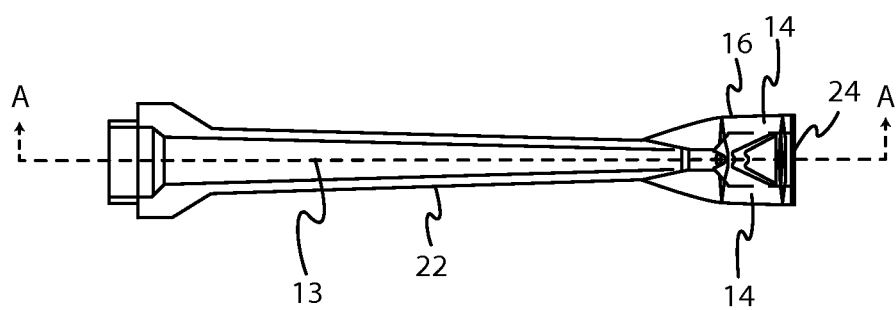
FIG. 5 is a bottom view of the arm of one embodiment of a surgical elevator with suction functionality.
Figure 6:
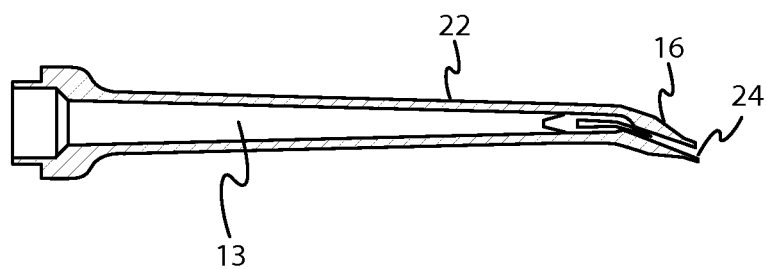
FIG. 6 is a cross-section view through section A-A of FIG. 5.

FIG. 5 provides a bottom view of the embodiment of arm 22 depicted in FIG. 4. Blade 16 and opening 24 are again shown. Central bore 13 is represented by dashed lines, and in the embodiment shown, the internal diameter of central bore 13 constricts along the length of arm 22 as it nears blade 16, whereupon central bore 13 widens and flattens to form opening 24. FIG. 6 provides a cross-section view of the embodiment of arm 22 shown in FIG. 5.

Figure 7:
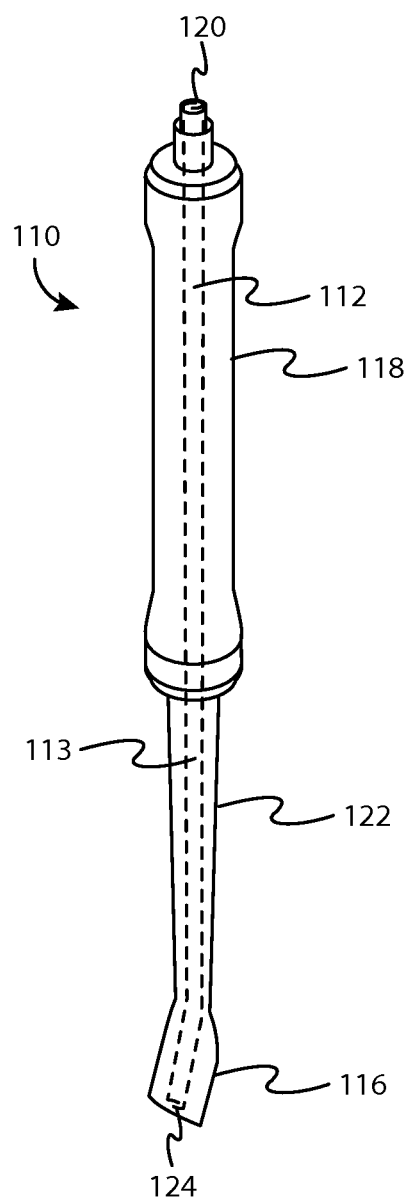
FIG. 7 is a perspective view of one alternate embodiment of a surgical elevator with suction functionality, with internal bores represented by dashed lines.

FIG. 7 provides a perspective view of one alternative embodiment of the present device—suction elevator 110, which include central bores 112 and 113 extending therethrough shown by dashed lines. As with suction elevator 10, suction elevator 110 includes a handle 118 having a central bore 112 extending therethrough. At one end of handle 118, connector 120 is provided, the connector also having a central bore extending therethrough, the central bore of the connector in fluid communication with central bore 112 of handle 118. The other end of handle 118 is attached to arm 122, which includes a central bore 113 extending along the length thereof and which terminates in opening 124. The embodiment of suction elevator 110 shown in FIG. 7 has a relatively small opening 124 positioned at the center of the tip of blade 116. The smaller opening 124 provides a narrower range of suction than does the opening 124 in embodiment 110 of the present suction elevator. The central, and narrower opening 124 also allows for wider flange areas flanking central bore 113 and opening 124 of blade 116 or, alternatively, rounded or otherwise shaped areas for this portion of blade 116. Thus, the profile of blade 116 may be shaped for a variety of purposes where a single point of suction in required in an elevator, but where other shapes flanking the suction point are desired.

Figure 8:
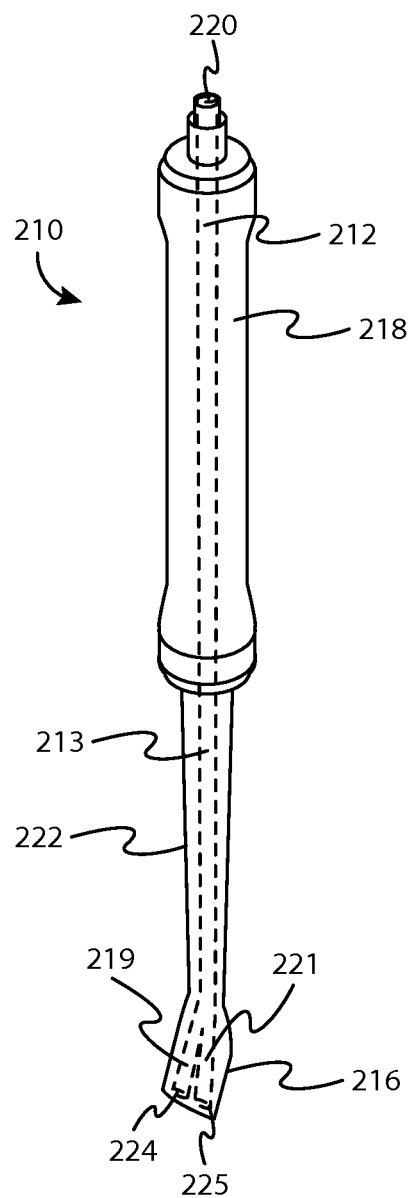
FIG. 8 is a perspective view of a second alternate embodiment of a surgical elevator with suction functionality, with internal bores represented by dashes lines.

FIG. 8 provides a view of another embodiment 210 of the present suction elevator. Suction elevator 210 includes the various common components of the present suction elevator, described above, including handle 218 and arm 222. Handle 218 has a connector 220 formed at one end thereof, a bore through connector 220 being in fluid communication with central bore 212 extending through the length of handle 218. Central bore 212 is in fluid communication with central bore 213 or arm 222, arm 222 being attached to the opposite end of handle 218 from connector 220. Central bore 213 extends along the length of arm 222 until, at or near the point where arm 222 forms blade 216, central bore 213 branches to form first terminal bore 219 and second terminal bore 221. The two terminal bores continue through arm 222 of surgical elevator 210 to form openings 224 and 225, respectively, in the end of blade 216. The end result is that the bore through suction elevator 210 defines a forked path, beginning as a single bore at the handle end of suction elevator 210 and forking to produce two bores at the blade end of suction elevator 210. The outer edges of the terminal bores are preferably in approximately in the same location as the outer edges of opening 24 described with respect to elevator 10, above. Thus, the flanges flanking central bore 213, terminal bores 219 and 221, and openings 224 and 225, are also as described above. It is contemplated, however, that the positions of openings 224 and 225 may be varied as needed or desired, and that the shape or profile of the flanking regions of blade 216 may also be varied as necessary or desirable.

It is contemplated that suction elevators 10, 110, and 210 may be constructed of any suitable material, including steel, aluminum, carbon fiber, or synthetic polymer. In some cases, the materials used may be such that the suction elevator can be sterilized by autoclave, and in other instances disposable materials may be used. Such materials should have the requisite strength, at thicknesses used in manufacture of the present device, to provide a strong, rigid device for separation of large muscle groups in a patient, such as the spinal muscles that must be separated during spinal surgery.

Connectors 20, 120, and 220 may be integrally formed with the suction elevator, or may be removable attachments that are disengaged from the surgical elevator when the device is to be cleaned or sterilized. For example, in FIG. 3, handle 12 is shown as having a first male connection 26 and a second male connection 28. First male connection 26 engages with female connection 30 of arm 22, and second male connection 28 engages with female connection 32 of connector 20. When the various connections are made up, a complete device is formed. In some embodiments, the arm 22, handle 18, and connector 20 may be permanently attached such that the surgical elevator 10 may not be disassembled by a user thereof. Arm 22, handle 18, and connector 20 may, for example, be attached to one another by an adhesive. Alternatively, in some embodiments of surgical elevator 10, the arm 22 and connector 20 may be detachable from handle 18 such that the surgical elevator 10 may be disassembled by a user thereof. It should also be noted that while male and female connections may be used, as shown in the drawings, any suitable attachment mechanism may be used, including, for example, mating threaded connections and the like. Any attachment mechanism used should be sufficient to preserve the force of suction drawn through the device when in use. Further, surgical elevator 10 may be constructed of a single, unitary piece of material such as molded polymer, steel, carbon fiber, and the like. Alternatively, different portions of surgical elevator 10 may be constructed of different materials.

It is further contemplated that the central bores 12, 13, 112, 113, 212, and 213 are formed in the material used to construct the surgical elevator, and can be utilized without any lining or other material being inserted into the surgical elevator. In some embodiments of the device, however, tubing or a polymer lining may be employed, with the tubing or lining being disposable between uses of the surgical elevator.

It is contemplated that the openings 24, 124, 224, and 225 are formed at or near the tip of the suction elevator. This allows for precise placement of suction during a surgical procedure and minimal disturbance of the surgical environment. While bores 12, 13, 112, 113, 212, and 213 are generally of continuous diameter along their lengths, it is contemplated that the internal diameter of the bores may be altered along their lengths in any way necessary or desirable to achieve a given purpose.

It is understood that the foregoing description and accompanying drawings are exemplary of the principles of the present device. Various modifications to the teachings herein will be readily apparent to one of skill in the art upon reading this disclosure, and it is understood that such modifications remain within the spirit and scope of present claims.

The invention claimed is:

1. A surgical elevator with suction capability comprising:
 a handle comprising a first end and a second end, and a connector at the first end thereof, the connector configured for attachment to a suction source;
 an arm extending from the second end of the handle, the arm comprising a blade portion at an end thereof opposite an end extending from the handle, the blade portion comprising a first, sharp side edge and a second, opposing sharp side edge,
 wherein the connector, handle, and arm define a continuous bore along the length of said surgical elevator, and further wherein the blade portion defines a single, continuous, uninterrupted opening in fluid communication with the bore.

2. The surgical elevator according to claim 1, wherein the handle, connector, and arm are comprised of a single, unitary piece of material.

3. The surgical elevator according to claim 1, wherein the bore comprises an internal diameter that decreases along the length of the handle.

4. The surgical elevator according to claim 3, wherein the bore further comprises an internal diameter that decreases along the length of the arm.

5. The device according to claim 1, wherein the bore branches at or near the blade portion of the device such that the blade portion defines a first terminal bore and a second terminal bore, and further wherein the opening defined by the blade is a first opening in fluid communication with the first terminal bore, the blade portion further defining a second opening in fluid communication with the second terminal bore.

6. The device according to claim 1, wherein the blade portion comprises a first flange at a first edge of the blade portion and a second flange at a second edge of the blade portion, the first and second flanges flanking at least a portion of the continuous bore running through the blade portion, and further wherein the first flange and second flange each comprises a flat, sharp edge.

7. The device according to claim 1, where the device has sufficient rigidity and structural strength to allow a user thereof to separate large muscle groups during a surgical procedure.

8. A surgical elevator with suction capability comprising:
 a handle comprising a first end and a second end and defining a first central bore therethrough;
 a connector attached to the first end of the handle and defining a second central bore therethrough, the second central bore in fluid communication with the first central bore, the connector configured for attachment to a suction source;
 an arm attached to the second end of the handle and defining a third central bore therethrough, the third central bore in fluid communication with the first central bore, the arm further defining a sharp flattened blade portion at an end thereof, the blade portion comprising a first sharp side edge and a second, opposing sharp side edge and defining an opening in fluid communication with the third central bore and an environment external to the surgical elevator.

* * * * *